United States Patent [19]

Halpaap et al.

[11] Patent Number: 5,071,938
[45] Date of Patent: Dec. 10, 1991

[54] POLYISOCYANATES, A PROCESS FOR THEIR PREPARATION AND THEIR USE IN STOVING LACQUERS

[75] Inventors: Reinhard Halpaap, Odenthal-Glöbusch; Wilhelm Dünwald, Leverkusen; Holger Casselmann, Bergisch Gladbach; Hans Schlegel, Leverkusen, all of Fed. Rep. of Germany

[73] Assignee: Bayer Aktiengesellschaft, Leverkusen, Fed. Rep. of Germany

[21] Appl. No.: 586,478

[22] Filed: Sep. 21, 1990

[30] Foreign Application Priority Data

Sep. 27, 1989 [DE] Fed. Rep. of Germany ....... 3932168

[51] Int. Cl.$^5$ .............................................. C08G 18/80
[52] U.S. Cl. .................................... 528/45; 428/425.8
[58] Field of Search ......................... 528/45; 428/425.8

[56] References Cited

U.S. PATENT DOCUMENTS

| | | | |
|---|---|---|---|
| 4,198,328 | 4/1980 | Bertelli et al. | 260/22 |
| 4,348,512 | 9/1982 | Grogler et al. | 528/73 |
| 4,384,102 | 5/1983 | Rasshofer et al. | 528/73 |

FOREIGN PATENT DOCUMENTS

| | | |
|---|---|---|
| 2938309 | 4/1981 | Fed. Rep. of Germany . |
| 59-041320 | 3/1984 | Japan . |
| 2177710 | 1/1987 | United Kingdom . |

OTHER PUBLICATIONS

T. Yamamoto et al., Kinetics of Carboxylic Acid . . . , Journal of Coatings Tech., vol. 60, pp. 51–99, 1988.

Z. W. Wicks, Progress in Organic Coatings, vol. 3, 1975, 73–99.
Z. W. Wicks, New Developments in the Field of Blocked Isocyanates, Progress in Organic Coatings, vol. 9, 1981, 3–28.

*Primary Examiner*—Maurice J. Welsh
*Attorney, Agent, or Firm*—Joseph C. Gil; Thomas W. Roy

[57] ABSTRACT

This invention relates to polyisocyanates containing
(i) 0.5 to 15% by weight of structural units incorporated by urea groups and corresponding to the formula

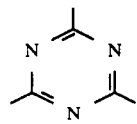

(ii) 5 to 20% by weight of isocyanate groups (calculated as NCO) reversibly blocked with monofunctional blocking agents for isocyanate groups and
(iii) 0 to 30% by weight of chemically incorporated urethane groups (calculated as NH—CO—O) other than urethane groups present in blocked isocyanate groups.

The invention also relates to a process for the preparation of these polyisocyanates and to their use in combination with organic polyhydroxyl compounds as stoving compositions or for the preparation of stoving compositions for heat resistant substrates, in particular wire.

10 Claims, No Drawings

POLYISOCYANATES, A PROCESS FOR THEIR PREPARATION AND THEIR USE IN STOVING LACQUERS

BACKGROUND OF THE INVENTION

1. Field of the Invention

The present invention relates to new polyisocyanates containing reversibly blocked isocyanate groups and also 1,3,5-triazine structural units incorporated by urea groups, to a process for the preparation of these polyisocyanates and to their use in combination with organic hydroxyl compounds as stoving lacquers.

2. Description of the Prior Art

It is known to use 1,3,5-triazine derivatives, in particular melamine, as starting materials for the preparation of binders for coating compositions. Thus, N-methylolmelamine resins and alkoxylated derivatives thereof are known as cross-linking agents for coating compositions; see, for example, T. Yamamoto, T. Nakamichi and O. Ohe in J. of Coat. Technology 60, 51 (1988) or H. Dürr and M. Schön in Kunstharznachrichten 45, 17 (1986).

It is also known to use melamine as a component of polyurethane resins or polyurethane coating compositions. Thus, isocyanate group-containing addition products of melamine and aromatic diisocyanates are described as incorporable fillers in DE-OS 2 737 402.

EP-A-56 153, on the other hand, describes epoxide group-containing compounds prepared from melamine-containing triisocyanates and glycidyl ethers as fillers with reduced melting points and improved compatibility which may be incorporated in polyurethane resins.

According to DE-OS 2 938 309, isocyanate prepolymers are reacted with free melamine used in the form of a polyester/melamine paste for the preparation of duroplastic coatings which have exceptionally good adherence to glass bottles.

Duroplastic resins prepared e.g. from diphenylmethane diisocyanate and melamine are described in DE-OS 3 609 687. Polycarbodiimide/melamine mixtures in the form of foams or powders which harden at 230° C. to form heat resistant and flame resistant resins are prepared by a process including carbodiimidization of the isocyanate.

According to DE-OS 2 844 132, for example, reaction products of diisocyanates and melamine at an NCO/NH$_2$ equivalent ratio of 1:1 are used as components for flame retardant coating compositions and according to Japanese Application JP 59 041-320 (Derwent 84-096 976) they are used as heat resistant resins.

Blocked polyisocyanates are also known. They are widely used in polyurethane chemistry for the production of polyurethane coating compositions. A comprehensive account of the chemistry of blocked isocyanates is given, for example, by Z. W. Wicks in Progress of Organic Coatings 3, 73–99 (1975) and 9, 3–28 (1981).

Polyisocyanates containing 1,3,5-triazine groups are high melting compounds which are difficult to dissolve in conventional organic solvents; see DE-OS 2 737 402, page 7, lines 23–25 and page 8, lines 15–19; EP-A-56 153, page 1, lines 12–15 and page 7, lines 24–27; and DE-OS 3 609 687, page 15, lines 18–20.

Although the incorporation of 1,3,5-triazine structural elements in many cases imparts advantageous properties to polyurethane resins and although there have been many attempts, as may be seen from the previously mentioned prior art, to make use of the advantageous properties of 1,3,5-triazine structural units in polyurethanes, polyisocyanates containing 1,3,5-triazine groups have previously hardly been used due to their high melting points and their poor solubility in organic solvents. Products which form clear solutions in conventional, physiologically harmless solvents are particularly in demand as coatings raw materials.

It is an object of the present invention to provide polyisocyanates which contain 1,3,5-triazine structural units and do not suffer from the disadvantages mentioned above. It is an additional object of the present invention to provide polyisocyanates which contain 1,3,5-triazine structural units and which have a low melting range and are soluble in conventional lacquer solvents. It is a further object of the present invention to provide polyisocyanates which contain 1,3,5-triazine structural units and which may be prepared by a simple process and react in the form of a solution or soluble, solid resin with isocyanate reactive compounds, in particular with polyhydroxyl compounds, to form high quality polyurethane resins, in particular coatings.

This object may be achieved in accordance with the present invention with the polyisocyanates described below. The term "polyisocyanates" is used in the context of this invention to denote both polyisocyanates, i.e., specific, individual compounds containing blocked isocyanate groups, and mixtures of polyisocyanates containing blocked isocyanate groups, which may be obtained by carrying out the process according to the invention.

The invention is based on the surprising observation that blocked polyisocyanates containing 1,3,5-triazine structural elements have a lower melting point and are more soluble in conventional lacquer solvents than the corresponding unblocked polyisocyanates. This fundamental difference between the blocked isocyanates and the unblocked polyisocyanates was not expected since it is not generally observed in the known polyisocyanates used in polyurethane chemistry.

SUMMARY OF THE INVENTION

This invention relates to polyisocyanates containing
(i) 0.5 to 15% by weight of structural units incorporated by urea groups and corresponding to the formula

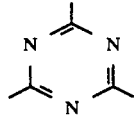

(ii) 5 to 20% by weight of isocyanate groups (calculated as NCO) reversibly blocked with monofunctional blocking agents for isocyanate groups and (iii) 0 to 30% by weight of chemically incorporated urethane groups (calculated as NH—CO—O) other than urethane groups present in blocked isocyanate groups.

The invention also relates to a process for the preparation of these polyisocyanates by reacting a) organic diisocyanates having a molecular weight of 160 to 300 with b) monofunctional, reversible blocking agents for isocyanate groups, c) triazines containing amino groups and corresponding to the formula

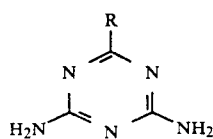

wherein

R represents an amino group or an isocyanate inert substituent and d) optionally organic polyhydroxyl compounds having a molecular weight of 62 to 3000, wherein i) blocking agent b) is used in an amount sufficient to block 20 to 90% of the isocyanate groups of component a)

ii) components c) and d) are used in a quantity corresponding to an equivalent ratio of the free isocyanate groups present after the blocking reaction to amino and hydroxyl groups of 0.65:1 to 1.05:1 and iii) the equivalent ratio of amino groups in component c) to hydroxyl groups in component d) is 1:0 to 1:20.

Finally, the present invention relates to the use of the polyisocyanates in combination with organic polyhydroxyl compounds as stoving compositions or for the preparation of stoving compositions for heat resistant substrates, in particular wire.

DETAILED DESCRIPTION OF THE INVENTION

In the process according to the invention for the preparation of the new polyisocyanates containing blocked isocyanate groups, monomeric starting diisocyanates a) are reacted with blocking agents b), 1,3,5-triazine derivatives c) and optionally organic polyhydroxyl compounds d) in an isocyanate addition reaction. "Blocked isocyanate groups" are produced by reaction with the blocking agents b) which are monofunctional and reversible in their reaction with isocyanate groups, and the term "urethane groups" refers only to the urethane groups formed by the reaction with polyhydroxyl compounds d).

The quantity of blocking agent b) is calculated to be sufficient to block 20 to 90%, preferably 35 to 80% and more preferably 50 to 70% of the isocyanate groups present in the starting diisocyanates. The quantity of components c) and d) is calculated to provide an equivalent ratio of the isocyanate groups present in component a) in excess of the blocking agents b) to the amino and hydroxyl groups in components c) and d) of 0.65:1 to 1.05:1, preferably 0.8:1 to 1.0:1. The equivalent ratio of the amino groups in component c) to the hydroxyl groups in component d) is 1:0 to 1:20, preferably 1:0 to 1:4, most preferably 1:0 to 1:1.

The starting diisocyanates a) include aromatic, aliphatic or cycloaliphatic diisocyanates having a molecular weight of 160 to 300 such as 1,4-phenylene diisocyanate, 2,4- and/or 2,6-diisocyanato-toluene (TDI), diphenylmethane-2,4'- and/or 4,4'-diisocyanate, 1,5-naphthylene diisocyanate, 2-methylpentane-1,5-diisocyanate, 1,5-hexane diisocyanate, 1,6-hexane diisocyanate (HDI), 1,3- and/or 1,4-cyclohexane diisocyanate, 3,5,5-trimethyl-3-isocyanatomethyl-cyclohexane isocyanate (IPDI), dicyclohexylmethane-2,4'- and/or -4,4'-diisocyanate and mixtures of these diisocyanates.

Preferred diisocyanates include 2,4-diisocyanatotoluene and 2,6-diisocyanatotoluene, the commercial isomeric mixtures of these diisocyanates, 4,4'-diisocyanato-diphenylmethane and 2,4'-diisocyanato-diphenylmethane, mixtures of these isomers, and mixtures of the aromatic diisocyanates mentioned here.

The blocking agents b) include any of the monofunctional compounds conventionally used for blocking isocyanate groups, such as those mentioned in Progress in Organic Coatings by Z. W. Wicks, 3, 73 et seq (1975) and 9, 3 et seq (1981). Phenols, aliphatic alcohols, oximes and lactams are preferred. Examples of suitable blocking agents b) include phenol, cresol, xylenol and commercial isomeric mixtures thereof, isopropanol, cyclohexanol, 1-methoxy-2-propanol (MP), diethylene glycol monoethyl ether, benzyl alcohol, butanone oxime, cyclohexanone oxime and $\epsilon$-caprolactam. Phenol cresol 1-methoxy-2-propanol, butanone oxime and $\epsilon$-caprolactam are particularly preferred.

The 1,3,5-triazines derivatives c) used include compounds corresponding to the formula

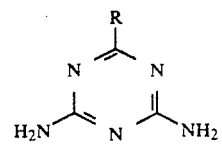

wherein

R represents an isocyanate inert organic group, preferably a $C_1$-$C_4$-alkyl, phenyl or $C_1$-$C_6$-alkoxy group and more preferably, an amino group.

Melamine is a particularly preferred 1,3,5-triazine derivative c).

The polyhydroxyl compounds d) which may optionally be used in accordance with the present invention are preferably diols and/or triols having a molecular weight of 62 to 350; however, higher molecular weight polyhydroxyl compounds having molecular weights above 350 and up to 3000 may also be used.

Examples of suitable polyhydroxyl compounds having a molecular weight of 62 to 350 include ethylene glycol, propanediols, butanediols, hexanediols, di-, tri- and tetraethylene glycol, di-, tri- and tetrapropylene glycol, neopentyl glycol, 2-ethyl-1,3-hexanediol, 2,2,4-trimethyl-1,3-pentanediol, 1,4-bis(hydroxymethyl)-cyclohexane, 2,2-bis(4-hydroxycyclohexyl)propane, trimethylolpropane, glycerol, hexanetriol, N,N',N"-tris-(2-hydroxyethyl)-isocyanurate (THEIC) and pentaerythriol.

Examples of relatively high molecular weight polyhydroxyl compounds which may be used but are less preferred include the known polyhydroxy polyesters obtained by reacting dicarboxylic acids such as phthalic acid, isophthalic acid, terephthalic acid or adipic acid with excess quantities of polyols such as those mentioned above. Known polyhydroxy polyethers which may be obtained by the alkoxylation of low molecular weight starter molecules may also be used but are also less preferred.

Mixtures of the above mentioned starting materials may, of course, also be used for carrying out the process according to the invention.

In the process according to the invention, the starting materials b), c) and optionally d) may be reacted in any sequence with diisocyanate component a). However, component c) is preferably not reacted with component a) before components b) and d). This means that, for example, a) may be reacted in a single stage with a mixture of b), c) and d) or a) may first be reacted with b) or with d) or with a mixture of b) and d) and subsequently with c) or with mixtures of c) and b) or mixtures of c) and d).

The above mentioned reactions are generally carried out at a temperature of 20° to 200° C., preferably 60° to 180° C.

In a preferred embodiment of the process according to the invention, the starting diisocyanate a) is blocked with blocking agent b) in the given quantitative ratio. The blocking reaction is carried out at a temperature of 20° to 200° C., preferably 60° to 160° C., depending upon the nature of the blocking agent, and is continued until the isocyanate content has been reduced to the theoretical level or slightly below. After termination of the blocking reaction, a solvent is added if a dissolved end product is to be produced, and the reaction of the partially blocked diisocyanate with melamine c), which is optionally added as a mixture with the polyol d), is carried out in a second reaction stage at a temperature of 60° to 180° C., preferably at 80° to 160° C. At this stage of the reaction, the polyol d), if used, generally reacts first at about 80° C. and then melamine reacts at a higher reaction temperature, preferably at about 140° C. The reaction is complete when a clear solution has been obtained or when the solvent-free resin can form a clear solution, e.g. in acetone, and the content of free isocyanate groups in the product has fallen to below 0.5% by weight.

This preferred variation of the process may be used for the preparation of polyisocyanates according to the invention as solutions in lacquer solvents or as solvent-free resins which generally solidify from the molten state as solid resins.

In another embodiment of the process according to the invention, the blocking reaction which constitutes the first reaction step is carried out in the presence of a suitable solvent and is followed by the reactions with the other reactants in accordance with the preferred embodiment described above.

In another embodiment of the process according to the invention diisocyanate a) is reacted with a mixture of blocking agent b), melamine c) and optionally polyol d) in a one-shot reaction. In this embodiment the aliphatic polyol reacts first at 60° to 90° C., the phenolic blocking agent preferably used subsequently reacts at 90° to 120° C. and the reaction with the melamine finally takes place at 120° to 140° C. The various reaction stages overlap and their progress can generally be followed by the decrease in exothermic heat evolved as the reaction reaches completion.

It is only in exceptional cases and by no means preferred that diisocyanate a) may first be reacted with melamine c) and optionally the polyol d) until the theoretical isocyanate content is reached, followed by blocking the remaining isocyanate groups with the blocking agent b).

The process according to the invention is generally carried out in solution although it may be carried out solvent-free, depending upon the properties of the desired end product, e.g., the degree of branching and the melt viscosity.

The solvents used include known lacquer solvents which are inert to isocyanate groups such as ethyl acetate, butyl acetate, ethylene glycol monomethyl ether acetate or monoethyl ether acetate, 1-methoxypropyl-2-acetate, 2-butanone, 4-methyl-2-pentanone, cyclohexanone, toluene, xylene, solvent naphtha and mixtures of these solvents. Plasticizers based on phosphoric, sulphonic or phthalic acid esters may also be used as solvents but are less preferred. A certain proportion of isocyanate reactive solvents may also be used in addition to the isocyanate inert lacquer solvents. These isocyanate reactive solvents are added only when the reaction has been completed or almost completed, e.g., when an isocyanate content of $\leq 0.5\%$ has been reached. This means that the polyisocyanates, which have been prepared mainly in the absence of such solvents, may be dissolved in such solvents after their preparation. Preferred solvents include monofunctional aliphatic, cycloaliphatic and araliphatic alcohols as well as phenols. Examples of these solvents include aliphatic alcohols such as isopropanol, n-butanol, n-octanol, 2-methoxyethanol, 2-ethoxyethanol, diethylene glycol monomethylether, diethylene glycol monoethylether and 1-methoxy-2-propanol; cycloalkanols such as cyclopentanol or cyclohexanol; aralkanols such as benzyl alcohol; and phenols such as cresol or xylenol.

Since the monohydric alcohols and phenols which are suitable as solvents may also be used as blocking agents b), it is apparent that when such alcohols or phenols are used as solvents, they are not included in the calculation of the proportions of reactants a) to d) when they are used as solvents after the reaction according to the invention has been completed.

The polyisocyanates according to the invention are valuable reactants for organic polyhydroxyl compounds and may be used in combination with such polyhydroxyl compounds as stoving lacquers or for the preparation of stoving lacquers for any heat resistant substrates. Suitable polyhydroxyl compounds for the preparation of such coating compositions include, for example, the compounds mentioned as examples under 1 to 5 below or any mixtures of such compounds:

1. Low molecular weight polyhydric alcohols having a maximum molecular weight of 350 and a hydroxyl functionality of 2 to 4 such as those already exemplified above as polyols d) and also 2,2-bis-[4-(2-hydroxyethoxy)-phenyl]propane, 2,2-bis-[4-(2-hydroxypropoxy)-phenyl]propane, maleic acid-bis-ethylene glycol ester and adipic acid-bis-ethylene glycol ester.

2. Relatively high molecular weight polyhydroxyl polyesters having a molecular weight of 351 to 4000 and obtained by the reaction of polybasic carboxylic acids such as adipic acid, phthalic acid, tetrahydrophthalic acid, hexahydrophthalic acid or their anhydrides with excess quantities of the polyhydric alcohols set forth under 1.

3. Aliphatically bound, hydroxyl-containing oligourethanes having a molecular weight of 200 to 2000 and obtained by reacting the alkanediols or -triols set forth under 1, which may contain ether groups, with subequivalent quantities of the starting diisocyanates a), such as the oligourethanes described e.g. in DE-PS 1 644 794 or in GB-PS 1 195 886.

4. Hydroxyl-containing copolymers obtained by the copolymerization of, for example, hydroxyalkyl acrylates or methacrylates with acrylic or methacrylic acid alkyl esters and optionally other olefinically unsaturated monomers and those obtained according to DE-OS 2 137 239 from styrene/maleic acid copolymers by partial esterification of the acid groups with ethylene oxide.

5. Hydroxyl-containing polycarbonates which are known and obtained, for example, by the reaction of diols such as 1,3-propanediol, 1,4-butanediol, 1,6-hexanediol and/or di-, tri- and/or tetraethylene glycol with phosgene or diaryl carbonates such as diphenyl carbonate, preferably polycarbonates based on 1,6-hexanediol and optionally about 5 to 35 mole percent of other diols which have a modifying action. Polycarbonates based on HO—(CH$_2$)$_6$—O—CO—(CH$_2$)$_5$—OH may also be used.

The compounds set forth under 2 and 3 above are the preferred reactants to be used with the polyisocyanates having blocked isocyanate groups according to the invention for the preparation of stoving lacquers. In addition to the reactants exemplified above, however, the stoving lacquers may contain other isocyanate reactive compounds, although these are generally less preferred. Examples of these include hydroxyl-containing oligomeric epoxides, imide esters, imido ester amides, hydantoins and compounds containing amino groups, such as hexamethylene diamine, melamine/formaldehyde resins and aminopolyethers.

The macroscopic properties of the coatings obtained according to the invention may easily be varied by suitable choice of the molecular weight of the polyhydroxyl compounds used. Thus relatively high molecular weight polyhydroxyl compounds generally result in more flexible coatings, while low molecular weight polyhydroxyl compounds result in harder coatings.

In accordance with the invention, the polyisocyanates are combined with the polyhydroxyl compounds set forth above in proportions which provide 0.1 to 10, preferably 0.2 to 2 and more preferably 0.5 to 1.2 hydroxyl groups in the hydroxyl-containing reactive component for each blocked isocyanate group in the polyisocyanates according to the invention.

The mixtures of the polyisocyanates according to the invention with the polyhydroxyl compounds set forth above may be used as such as stoving lacquers but they may also be mixed first with auxiliary agents and additives such as solvents, catalysts, pigments and the like.

Suitable solvents include in particular those already mentioned above as examples. When monohydric alcohols or phenols are used as solvents, they are displaced by the non-volatile polyhydroxyl compounds in the course of the stoving process so that they are distilled from the reaction mixture together with the blocking agent during the stoving process. For wire lacquering, which is a preferred use according to the invention, the compositions of polyisocyanates and polyhydroxyl compounds are generally used in the form of 15 to 75% by weight solutions, in particular from 20 to 60% by weight solutions.

Examples of catalysts which may be used according to the invention are described in Kunststoffhandbuch (published by Becker/Braun), Vol. 7, Polyurethane, pages 92 et seq, Carl Hanser Verlag, Munich, Vienna 1983. The catalysts described in DE-AS 2 626 175, column 7, line 35 to column 8, line 27, for example, are also suitable. Organic metal catalysts are particularly suitable, in particular organic titanium, zinc or tin compounds, such as tetraisopropyltitanate, zinc octoate, dibutyl tin oxide or dibutyl tin dilaurate.

The catalysts, if used, are introduced in a quantity of 0.01 to 5.0% by weight, preferably 0.1 to 3.0% by weight, based on the blocked polyisocyanates according to the invention.

The mixtures obtained by mixing the above-mentioned essential components of the invention and auxiliary agents and additives at room temperature are stable in storage at room temperature or moderately elevated temperatures (up to about 50° C.). When heated to temperatures above 60° C., preferably 100° to 500° C., most preferably 180° to 400° C., they react to form cross-linked synthetic resins. The reaction is accompanied by evaporation of any volatile components present (e.g. solvents). The stoving lacquers prepared from the polyisocyanates according to the invention are suitable for coating any heat-resistant substrates, preferably glass fibers and more preferably metal wires. The stoving lacquers may be applied to the substrates by any of the known methods of coating technology and the coatings obtained are then cured within the above mentioned temperature ranges.

In the preferred use according to the invention of coating wires, the wires are coated by the known dip coating, roller application or suction felt process, wherein drying, i.e. hardening of the coating layers, is carried out in a drying oven within the temperature ranges stated. When the products according to the invention are used as cross-linking agents for wire lacquers, the excellent adherence to the wire and the high speed of lacquering which may be obtained when compared with those of conventional products known in the art are particularly outstanding.

Because of the excellent electrical and mechanical properties of the synthetic resins obtained in accordance with the present invention, the compositions of polyisocyanates according to the invention, polyhydroxyl compounds and optionally auxiliary agents and additives are also suitable for the production of insulating fabrics or for impregnating electric motors.

All percentages in the following examples are percentages by weight unless otherwise indicated. The blocked isocyanate group contents were calculated as "NCO," i.e., on the basis of a molecular weight of 42. The urethane group contents refer exclusively to the urethane groups formed by the reaction of isocyanate groups with polyhydric alcohols and do not include the blocked isocyanate groups formed from isocyanate groups and monovalent alcoholic or phenolic blocking agents, even though these blocked isocyanate groups are also urethane groups.

EXAMPLES

Example 1 a) Preparation 1537 parts by weight of cresol (commercial isomeric mixture) were added dropwise in the course of about one hour to 2064 parts by weight of diisocyanatotoluene (2,4- and 2,6-isomers in a ratio by weight of 8:2), starting at 80° C. and continuing while the diisocyanatotoluene was heated to 130° C. The mixture was left to react at 120° to 140° C. for about 8 to 15 hours until an isocyanate content of 11.0% was obtained (theoretical NCO=11.1%). The reaction mixture was dissolved in 5000 parts by weight of 1-methoxypropyl-2-acetate with cooling and a suspension of 399 parts by weight of melamine in 1000 parts by weight of 1-methoxypropyl-2-acetate was added at 80° C. The suspension was then rapidly heated to 140° C. with vigorous stirring. A clear solution was obtained after a reaction time of about 3 hours. After a further hour with stirring, the reaction was complete and the free isocyanate content was <0.1%.

A clear solution of the blocked isocyanate having the following properties was obtained (all data set forth here and in the following examples of preparation refer to the solution):

| | |
|---|---|
| Concentration: | 40% |
| Viscosity $\eta_{(23°\,C.)}$: | 28,000 mPa · s |
| Free NCO content: | <0.1% |
| Blocked NCO content: | 5.9% |
| (Analytical method: 30 min/180° C. using di-n-butylamine in o-dichlorobenzene) | |
| Blocked NCO content (calculated): | 6.0% |
| 1,3,5-triazine units (calculated): | 2.5% |
| Urethane groups (calculated): | 0% | b) Use

200 Parts by weight of a polyester having an OH number of 395 and prepared from 40.8% trimethylolpropane, 14.2% ethylene glycol and 45.0% phthalic acid anhydride were dissolved in 800 parts by weight of a solvent mixture of equal parts cresol and xylene under reflux at a temperature of up to 130° C. To the resulting solution were added 1000 parts by weight of the 40% solution of blocked polyisocyanate prepared as described in a) and 6 parts by weight of an aldimine based on butyraldehyde and aniline as catalyst.

A copper wire 0.7 mm in diameter was lacquered with the solution thus prepared.

| | |
|---|---|
| Lacquering oven: | vertical with felt stripper (6 passages through the oven) |
| Length of oven: | 4 m |
| Oven temperature: | 350° C. |
| Increase in diameter by lacquering: | 40-50 μm |
| Speed of lacquering: | 10-16 m/min. |

The lacquered wire thus obtained was soldered in 9 seconds at 320° C. and had a pencil hardness of 4H which remained unchanged even after immersion for one half hour in ethanol heated to 60° C.

When a conventional, commercially available lacquer system was used which differed from the described lacquer system according to the invention only in the nature of the hardener (i.e., an equivalent quantity of a blocked isocyanate based on the reaction product of 55.6% diisocyanatotoluene (2,4- and 2,6-isomers in a ratio by weight of 8:2), 14.3% trimethylolpropane and 30.1% phenol was used), the resulting coated wire either could not be soldered at 320° C. or the soldering time was much longer than 9 seconds. The pencil hardness fell to HB after treatment for one half hour in ethanol at 60° C.

Example 2 a) Preparation

A solution of 1408 parts of phenol in 3000 parts by weight of 1-methoxypropyl-2-acetate was added dropwise at 120° C. within about 30 minutes to 2172 parts by weight of diisocyanatotoluene (2,4- and 2,6-isomers in a ratio by weight of 8:2). The mixture was left to react for about 2 hours at 120° C. and cooled after an isocyanate content of 6.7% (theoretical NCO=6.4%) had been reached. A suspension of 419 parts by weight of melamine in a further 3000 parts by weight of 1-methoxypropyl-2-acetate was added at 40° C., which reduced the NCO content of the solution to 4.3%. The reaction mixture was heated to 140° C. with stirring. The mixture became clear after about 1.5 hours and the reaction was terminated after further stirring for one hour at 140° C.

A clear, pale yellow solution having the following properties was obtained:

| | |
|---|---|
| Concentration: | 40% |
| Viscosity $\eta_{(23°\,C.)}$ | 3,240 mPa · s |
| Free NCO content: | 0.4% |
| Blocked NCO content (found): | 6.6% |
| Blocked NCO content (calculated): | 6.3% |
| 1,3,5-triazine units (calculated): | 2.6% |
| Urethane groups (calculated): | 0% | b) Use 150 parts by weight of a hydroxyurethane having an OH number of 190 and prepared from 26.5% 1,6-hexanediol, 21.0% trimethylolpropane, 1.8% ε-caproiacuun and 50.7% diisocyanatotoluene (2,4- and 2,6-isomers in ratio by weight of 8:2) were dissolved in 475 parts by weight of a mixture of equal parts by weight of cresol and xylene at 130° C. under reflux and 375 parts by weight of the solution of blocked polyisocyanate prepared as described under a) were added after the hydroxyurethane had cooled. 3 parts by weight of an aldimine based on butyraldehyde and aniline (1% based on solids) were added as catalyst.

In a vertical wire coating machine having an oven 4 m in length, a copper wire 0.7 mm in diameter was lacquered by means of a felt stripper in six passes to provide a diameter increase of 50 μm. At an oven temperature was 350° C., the wire was lacquered at the rate of 10 to 20 m/min without the coating showing any cracks when the copper wire was stretched to the point of breakage. The lacquer wire obtained had a remarkably good abrasion resistance and can be soldered at 320° C. In tests for abrasion resistance by the NEMA method, the lacquered wire withstood more than 100 double strokes under a weight of 400 g).

When the polyisocyanate according to the invention was replaced by an equivalent quantity of the conventional hardener described in Example 1, the lacquer wire obtained under otherwise identical coating conditions either could not be soldered at 320° C. or the soldering time was considerably longer than 10 seconds, depending upon the degree of stoving. The abrasion resistance was considerably poorer and the wire withstood only about half the double strokes described above.

Example 3 a) Preparation

2589 Parts by weight of cresol (commercial isomeric mixture) were rapidly added to 2979 parts by weight of diisocyanatotoluene (2,4- and 2,6-isomers in a ratio by weight of 8:2) as the diisocyanatotoluene was heated from 80° C. to 130° C. An isocyanate content of 7.5% was obtained after about 12 hours. Thereafter, a solution of the reaction mixture was formed by the addition of 3000 parts by weight of 1-methoxypropyl-2-acetate. A suspension of 432 parts by weight of melamine in a further 1000 parts by weight of 1-methoxypropyl-2-acetate was added at a temperature below 80° C. After the suspension had been heated to 140° C., it became clear after the reaction had proceeded for about 2.5 hours and after further stirring for about one hour the reaction was terminated when the isocyanate content had been reduced to essentially zero.

A clear, dissolved product having the following properties was obtained:

| | |
|---|---|
| Concentration: | 60% |
| Viscosity $\eta_{(23°\ C.)}$: | 20,000 mPa · s |
| Free NCO content: | 0.1% |
| Blocked NCO content (found): | 9.9% |
| Blocked NCO content (calculated): | 10.1% |
| 1,3,5-triazine units (calculated): | 2.7% |
| Urethane groups (calculated): | 0% | b) Use 150 parts by weight of the hydroxyurethane described in Example 2b were dissolved under reflux in 600 parts by weight of a mixture of equal parts by weight of cresol and xylene at a temperature of less than 130° C. The solution obtained was mixed with 250 parts by weight of the solution of blocked isocyanate prepared as described above under a). 3 parts by weight of an aldimine based on butyraldehyde/aniline were then added as catalyst (1% based on solids) to the coating composition.

In a wire lacquering machine having an oven 4 m in length, a copper wire 0.7 mm in diameter was coated by means of a felt stripper in six passes lacquered to provide an increase in diameter of 50 μm. At an oven temperature of 400° C., the speed of the wire was varied from 8 m/min to 20 m/min. A perfectly coated wire was obtained within this range of stoving speeds.

The lacquer wire passed the test for cracking under water (hairline cracks), i.e., it was bent round a spindle 20 mm in diameter under water without forming hairline cracks. In this test, the wire was bent around a spindle with progressively decreasing diameter, starting at a diameter of 100 mm, in a 0.5% NaCl solution, and a direct voltage of 100 V was applied to the water bath and the copper conductor. No current flow was observed.

Example 4 a) Preparation

3085 Parts by weight of diisocyanatotoluene (2,4- and 2,6-isomers in a ratio by weight of 8:2) were blocked with 2298 parts by weight of cresol (commercial isomeric mixture) as described in Example 1a). When the NCO content had been reduced to 11.1% (theoretical NCO=11.1%), 4000 parts by weight of 1-methoxypropyl-2-acetate were added as solvent. When the clear solution had cooled to 60° C., a mixture of 298 parts by weight of melamine and 319 parts by weight of 1,3-butanediol was added and the mixture was left to react at 80° C. for 2 hours. The reaction mixture, which was still heterogeneous, was then heated to 140° C. and the reaction was terminated at this temperature when a clear solution was obtained.

| Properties: | |
|---|---|
| Concentration: | 60% |
| Viscosity $\eta_{(23°\ C.)}$: | 8,800 mPa · s |
| Free NCO content: | 0.2% |
| Blocked NCO content (calculated): | 8.9% |
| 1,3,5-triazine units (calculated): | 1.8% |
| Urethane groups (calculated): | 4.2% | b) Use

150 Parts by weight of the hydroxyurethane having an OH number 190 and described in Example 2b) were dissolved by heating in 600 parts by weight of a mixture of equal parts by weight of N-methylpyrrolidone and 1-methoxypropyl-2-acetate. The solution thus obtained was mixed with 250 parts by weight of the solution prepared as described under a) and 3 parts by weight of an aldimine based on butyraldehyde/aniline were added as calalyst.

In a wire coating machine having an oven 4 m in length and operated at an oven temperature of 400° C., a copper wire 0.7 mm in diameter was coated by means of a felt stripper in six passages to provide a diameter increase of 50 μm.

The lacquer wire thus produced had excellent adhesion to the wire. In the test according to DIN 46 453 8.4, more than 500 twists were made before the layer of lacquer showed the first signs of separating.

For comparison, a wire was lacquered under the same conditions as described above with the exception that the blocked polyisocyanate of Example 4a) according to the invention was replaced by an equivalent quainity of the commericially available blocked polyisocyanate described in Example 1b). In the test for bond strength according to DIN 46 453 8.4, the wire could only be twisted about 350 times. The strength of adhesion of the coating according to the invention was substantially greater.

Example 5 a) Preparation 1486 by weight of cresol (commercial isomeric mixture) were added to a diisocyanate mixture of 1197 parts by weight of diisocyanatotoluene (2,4- and 2,6-isomers in a ratio by weight of 8:2) and 1719 parts by weight of 4,4'-diisocyanatodiphenylmethane as the mixture was heated from 80° C. to 130° C. After about 8 hours at 130° C. and when an isocyanate content of 13.1% had been obtained (theoretical NCO=13.1%), 5000 parts by weight of 1-methoxypropyl-2-acetate were added and a mixture of 289 parts by weight of melamine and 309 parts by weight of 1,3-butanediol was introduced at 60° C. The mixture was left to react for 2 hours at 80° C. and 2 hours at 140° C. until a clear solution was obtained.

The clear, pale yellow solution had the following properties:

| | |
|---|---|
| Concentration: | 50% |
| Viscosity $\eta_{(23°\ C.)}$: | 17,500 mPa · s |
| Free NCO content: | <0.1% |
| Blocked NCO content (calculated): | 5.8% |
| 1,3,5-triazine units (calculated): | 1.8% |
| Urethane groups (calculated): | 4.1% | b) Use 150 parts by weight of the hydroxyurethane described in Example 2b) were dissolved in 550 parts by weight of a mixture of equal parts by weight of N-methylpyrrolidone and 1-methoxypropyl-2-acetate with heating to 130° C. After the solution had cooled, 300 parts by weight of the solution of blocked polyisocyanate prepared as described under a) above and 3 parts by weight of an aldimine based on butyraldehyde/aniline are added as catalyst.

In a wire coating machine having an oven 4 m in length and operating at an oven temperature of 400° C., a copper wire 0.7 mm in diameter was coated by means of a felt stripper in six passages to provide an increase in diameter of 50 μm.

The lacquer wire obtained had excellent resistance to hairline cracking. In the spindle bending test described in Example 3b), the lacquer wire was bent round a spindle of 20 mm without any hairline cracks appearing.

Example 6 a) Preparation 3297 parts by weight of diisocyanatotoluene (2,4- and 2,6-isomers in a ratio by weight of 8:2) were added dropwise at 80° C. to a mixture of 2046 parts by weight of 1-methoxy-2-propanol, 339 parts by weight of trimethylolpropane and 318 parts by weight of melamine over a period of about 20 minutes at such a rate that the temperature of the exothermic reaction was kept below 100° C. After about one hour as the reaction mixture became more viscous, it was heated to 110° C. for about 1.5 hours and then to 140° C. After about 2.5 hours, no free isocyanate could be detected. 4000 parts by weight of 1-methoxy-2-propanol were then added as solvent. The clear, colorless solution of the methoxypropanol-blocked polyisocyanate had the following properties:

| Concentration: | 60% |
|---|---|
| Viscosity $\eta_{(23° C.)}$: | 2,800 mPa · s |
| Free NCO content: | 0% |
| Blocked NCO content (calculated): | 9.5% |
| 1,3,5-triazine units (calculated): | 2.0% |
| Urethane groups (calculated): | 4.5% | b) Use 150 parts by weight of the hydroxyurethane described in Example 2b) were dissolved in 600 parts by weight of a solvent mixture of equal parts by weight of N-methylpyrrolidone and 1-methoxypropyl-2-acetate with heating to 130° C. After the solution had cooled, it was mixed with 250 parts by weight of the blocked polyisocyanate prepared as described under a) and 3 parts by weight of zinc octoate (Zn content=8%) were added as catalyst (1% based on solids).

In a wire coating machine having an oven 4 m in length and operating at an oven temperature of 400° C., a copper wire 0.7 mm in diameter was coated by means of a felt stripper in six passages to provide an increase in diameter of 50 μm. The speed of wire lacquering was varied from 12 m/min to 16 m/min.

The lacquered wire obtained was found to have heat shock resistance up to a temperature of 260° C., which is an excellent result. The heat shock test was carried out according to DIN 46 453 by winding the lacquered wire around a spindle having the same diameter as the wire (0.7 mm) to form turns in contact with one another. Three such coils are kept for 30 minutes in a cupboard which has been preheated to 260° C. The coating on the originally perfect coil was found to have no cracks or fractures after this test.

Example 7 a) Preparation 1782 parts by weight of butanone oxime, 215 parts by weight of melamine and 384 parts by weight of 1,3-butanediol were added to 2000 parts by weight of 1-methoxy-propyl-2-acetate. A solution of 1485 parts by weight of diisocyanatotoluene (2,4- and 2,6-isomers in a ratio by weight of 8:2) and 2134 parts by weight of 4,4'-diisocyanatodiphenylmethane in 2000 parts by weight of 1-methoxy-propyl-2-acetate was added dropwise within about one our beginning at 60° C. The reaction mixture, which was initially exothermic, was stirred for about 2 hours at 80° C. and then for one hour at 140° C. until no more free isocyanate were present and a clear solution was obtained.

The clear, yellow solution had the following properties:

| Concentration: | 60% |
|---|---|
| Viscosity $\eta_{(23° C.)}$: | 4,320 mPa · s |
| Free NCO content: | 0% |
| Blocked NCO content (calculated): | 8.6% |
| 1,3,5-triazine units (calculated): | 1.3% |
| Urethane groups (calculated): | 5.0% | b) Use 150 parts by weight of the hydroxyurethane described in Example 2b) were dissolved in 600 parts by weight of a solvent mixture of equal parts by weight of N-methylpyrrolidone and 1-methoxypropyl-2-acetate with heating to 130° C. After the solution had cooled, 250 parts by weight of the solution of blocked polyisocyanate described under a) were added. 3 parts by weight of zinc octoate (Zn content=8%) were added as catalyst.

A copper wire 0.7 mm in diameter was coated as described in Example 6b) under the same stoving conditions. The speed of wire coating was varied from 10 m/min to 16 m/min.

The product was found to be heat shock resistant as described in Example 6b) at temperatures up to 260° C., which again is an excellent result.

Example 8 a) Use 395 parts by weight of a mixture of equal parts by weight of cresol and xylene were added to 230 parts by weight of a 65% solution in 1-methoxypropyl-2-acetate of a hydroxyurethane prepared from 22.1% trimethylolpropane, 8.7% diethylene glycol, 7.4% 1,3-butanediol and 61.8% 4,4'-diisocyanatodiphenylmethane. 375 parts by weight of the solution of blocked polyisocyanate prepared as described in Example 1a were added and 3 parts by weight of an aldimine of butyraldehyde/aniline were added as catalyst.

In the wire lacquering machine described in the previous examples and operated at an oven temperature of 400° C., a copper wire 0.7 mm in diameter was coated using felt strippers in six passes to provide a diameter increase of 50 μm. The speed of coating was varied from 10 to 22 m/min. The lacquered wire obtained was distinguished by exceptionally high abrasion resistance. When placed under a weight of 380 g using the test procedure described in Example 2b, it withstood 120 double strokes. The lacquer wire had a good softening temperature and withstood a test temperature of 250° C. (DIN 46 453 10.1).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyisocyanate containing
   (i) 0.5 to 15% by weight of structural units incorporated by urea groups and corresponding to the formula

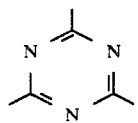

(ii) 5 to 20% by weight of isocyanite groups (calculated as NCO) reversibly blocked with a monofunctional blocking agent for isocyanate groups and (iii) 0 to 30% by weight of chemically incorporated urethane groups (calculated as —NH—CO—O—) other than urethane groups present in blocked isocyanate groups.

2. The polyisocyanate of claim 1 wherein the polyisocyanate contains less than 0.5% by weight of unreacted isocyanate groups.

3. A process for the preparation of a polyisocyanate which comprises reacting
   a) an organic diisocyanate having a molecular weight of 160 to 300 with
   b) a reversible, monofunctional blocking agent for isocyanate groups in an amount sufficient to block 20 to 90% of the isocyanate groups in component a) and to provide 5 to 20% by weight, based on the weight of said polyisocyanate, of blocked isocyanate groups (calculated as NCO),
   c) triazines containing amino groups corresponding to the formula

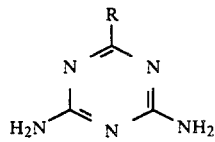

wherein
R represents an amino group or an isocyanate inert substituent,
in an amount sufficient to provide 0.5 to 15% by weight of structural units corresponding to the formula

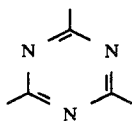

and
   d) organic polyhydroxyl compounds having a molecular weight of 62 to 3000 in an amount sufficient to provide an equivalent ratio of amino groups in component c) to hydroxyl groups in component d) of 1:0 to 1:20,
wherein components c) and d) are used in an amount which provides an equivalent ratio of isocyanate groups which are not blocked with blocking agent b) to amino and hydroxyl groups of 65:1 to 1.05:1.

4. A process of claim 3 wherein
   A) blocking agent b) is used in an amount sufficient to block 35 to 80% of the isocyanate groups of component a),
   B) the equivalent ratio of amino groups in component c) to hydroxyl groups in component d) is 1:0 to 1:4 and
   C) components c) and d) are used in an amount which provides an equivalent ratio of isocyanate groups which are not blocked with blocking agent b) to amino and hydroxyl groups of 0.8:1 to 1:1.

5. The process of claim 3 wherein blocking agent b) comprises a member selected from the group consisting of phenols, aliphatic alcohols, oximes and lactams.

6. The process of claim 3 wherein component c) comprises melamine.

7. The process of claim 3 wherein component d) comprises an aliphatic and/or cycloaliphatic polyhydric alcohol having a molecular weight of 62 to 350 which may contain ether bridges or an isocyanurate ring.

8. A process for the preparation of polyisocyanate which comprises reacting
   a) an organic diisocyanate having a molecular weight range of 160 to 300 are reacted with
   a) reversible, monofunctional blocking agent for isocyanate groups comprising a member selected from the group consisting of phenols, aliphatic alcohols, oximes and lactams in an amount sufficient to block 35 to 80% of the isocyanate groups in component a) and to provide 5 to 20% by weight, based on the weight of said polyisocyanate, of blocked isocyanate groups (calculated as NCO),
   c) melamine in an amount sufficient to provide 0.5 to 15% by weight of structural units corresponding to the formula

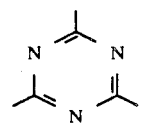

and
   d) an aliphatic and/or cycloaliphatic polyhydric alcohol having a molecular weight of 62 to 350 which may contain ether bridges or an isocyanurate ring in an amount sufficient to provide an equivalent ratio of amino groups in component c) to hydroxyl groups in component d) of 1:0 to 1:4,
wherein components c) and d) are used in an amount which provides an equivalent ratio of isocyanate groups which are not blocked with blocking agent b) to amino and hydroxyl groups of 0.8:1 to 1:1.

9. A process for coating a heat resistant substrate which comprises coating said substrate with a composition comprising the polyisocyanate of claim 1 and an organic polyhydroxyl compounds and curing said composition at elevated temperature.

10. The process of claim 9 wherein said heat resistant substrate is a wire.

* * * * *